US011439384B2

(12) United States Patent
Gittard et al.

(10) Patent No.: US 11,439,384 B2
(45) Date of Patent: Sep. 13, 2022

(54) SUTURE LOCK DEVICE

(71) Applicant: Muffin Incorporated, West Lafayette, IN (US)

(72) Inventors: Shaun Davis Gittard, Winston-Salem, NC (US); John C. Sigmon, Jr., Winston-Salem, NC (US); Gregory James Hardy, Asheville, NC (US); Michelle Martinez, Winston Salem, NC (US); Vihar C. Surti, Winston-Salem, NC (US); Jeremy T. Newkirk, West Lafayette, IN (US); William J. Havel, West Lafayette, IN (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 523 days.

(21) Appl. No.: 16/394,192

(22) Filed: Apr. 25, 2019

(65) Prior Publication Data

US 2019/0247043 A1    Aug. 15, 2019

Related U.S. Application Data

(63) Continuation of application No. PCT/US2017/058237, filed on Oct. 25, 2017.
(Continued)

(51) Int. Cl.
*A61B 17/04* (2006.01)
*A61B 17/00* (2006.01)

(52) U.S. Cl.
CPC ...... *A61B 17/0487* (2013.01); *A61B 2017/00367* (2013.01); *A61B 2017/0496* (2013.01)

(58) Field of Classification Search
CPC ............ A61B 17/0487; A61B 17/0401; A61B 2017/00367; A61B 2017/0496;
(Continued)

(56) References Cited

U.S. PATENT DOCUMENTS 11,096,449 B2 *   8/2021   Krout ................... A43C 11/24
2005/0222488 A1  10/2005   Chang et al.
(Continued)

FOREIGN PATENT DOCUMENTS

WO    WO 2015/193728 A2    12/2015

OTHER PUBLICATIONS

International Application No. PCT/US2017/058237 International Search Report and Written Opinion, dated Apr. 12, 2018, 16pgs.

*Primary Examiner* — Erich G Herbermann
(74) *Attorney, Agent, or Firm* — Woodard Emhardt Henry Reeves & Wagner LLP (57) ABSTRACT

Among other things, there are shown embodiments of locking mechanisms for holding sutures in tension. Such devices may be used with implants that use or require sutures, and are easily locked remotely. In particular embodiments, a lock includes a housing member, a pin member at least partially within the housing member, and a spring biasing the pin member into the housing member. The pin member includes a gripping portion, and has a retracted condition and a locked condition. When retracted, a suture can move through the housing member and around the gripping portion of the pin member. When locked, the gripping portion of the pin member engages the suture and presses it against the interior of the housing member.

21 Claims, 7 Drawing Sheets

Related U.S. Application Data (60) Provisional application No. 62/412,636, filed on Oct. 25, 2016.

(58) Field of Classification Search
CPC .... A61B 2017/0409; A61B 2017/0427; A61B 2017/0446; Y10T 24/3984; F16G 11/101; A61L 31/143; A61M 2025/09125; A61M 2025/09116; A61F 2/0811
See application file for complete search history.

(56) References Cited

U.S. PATENT DOCUMENTS

| | | | |
|---|---|---|---|
| 2010/0057110 A1* | 3/2010 | Lampropoulos ... | A61B 17/0485 606/148 |
| 2010/0257701 A1* | 10/2010 | Gammell ............ | A43C 1/00 24/115 G |
| 2011/0152889 A1 | 6/2011 | Ashland | |

* cited by examiner

SUTURE LOCK DEVICE

This disclosure concerns locks for maintaining tension on a suture. In particular, it concerns improved devices making such locking easier, particularly in a minimally-invasive procedure. This application is a continuation of PCT/US2017/058237, filed on Oct. 25, 2017 which claims the benefit of U.S. Provisional Application No. 62/412,636, filed Oct. 25, 2016, which is incorporated by reference in its entirety.

BACKGROUND

Manually tying suture strands together as part of a medical procedure, particularly a laparoscopic or otherwise minimally-invasive procedure, can be complex and time consuming. For example, a significant level of skill and coordination is required by the medical professional, especially when the perforation and sutures are difficult to access within the body, such as in endoscopic or laparoscopic procedures. The numerous difficulties with manually tying sutures are well documented. In order to address these and other issues of manual suture tying, various automatic suture tying systems have been developed. Unfortunately, such automatic systems are often complex and costly, difficult to use, and limited to use in certain situations.

The present disclosure includes a device that is used to lock a suture in a desired position and/or at a desired tension. Particular embodiments may be used to hold a suture that is a part of a particular implant, such as implants for placement in body locations having limited or difficult access, including but not limited to implants that are part of treatment of a cardiac condition.

SUMMARY

Among other things, there is disclosed a locking device for holding a suture in tension, that may include a housing member having a hollow interior with an interior end surface, a side wall and a first and second end. In particular embodiments, the side wall includes two opposed side openings. A pin member is partially within the hollow interior, and includes a gripping portion within the hollow interior and a shaft member fixed to the gripping portion. In some embodiments, a hole extends through the shaft member perpendicular to a longitudinal axis of the shaft member. A spring is within the hollow interior and around the shaft member, and may abut the gripping portion of the pin member and the interior end surface of the housing member. In particular embodiments, the device has a first unlocked condition in which the pin member is retracted and held against bias of the spring and the gripping portion is at a first location within the housing to a movement path for the suture (e.g. through at least one of the side openings), around the gripping portion of the pin member and through the first end of the housing member. In that first unlocked condition, a portion of the shaft extends through the second end of the housing member. In a second locked condition, the spring bias holds the pin member in a position in which the gripping portion is in a second position closer to the first end than the first position is to the first end, and which creates at least one pinch point between the gripping portion of the pin member and the housing member.

In some embodiments, the housing member includes a part-cylindrical exterior, with a flat surface extending from the first end to the second end. The side openings may be opposed to each other, and the flat surface is between the side openings. The pin member may have a bulbous tail portion on the shaft member opposite to the gripping portion, and the tail portion may have a maximum diameter greater than an external diameter of the shaft member. Such a tail portion may include an exterior longitudinal channel, which can be aligned with the flat surface of the housing. The tail portion may include a through hole perpendicular to the longitudinal axis of the shaft member. In some embodiments, the gripping portion of the pin member has an external diameter larger than an external diameter of the shaft member, and the hollow interior of the housing member can include a chamber having an interior diameter that allows the gripping portion to travel longitudinally within the chamber. A gripping portion may be in the form of a flange, e.g. having opposite facing first and second surfaces, a circumferential groove between the first and second surfaces, a first edge between the circumferential groove and the first surface, and a second edge between the circumferential groove and the second surface. A flange may include a circular portion and a flat side, the flat side oriented toward the flat surface of the housing member. The pin member may include a head portion connected to the first surface of the flange and collinear with the shaft, and the head portion may have a lip. A second circumferential groove may be between such a lip and the first surface of the flange. Other embodiments may have a gripping portion in the form of a bulbous head. In some embodiments, the first end of the housing includes a hole along the longitudinal axis and communicating with the hollow interior, with the hole having an inner diameter smaller than an outer diameter of the gripping portion. The first end of the housing can include a plurality of apertures perpendicular to the longitudinal axis and communicating with the hole. As examples, at least one of such apertures can be in the flat surface of the housing, and/or at least two of the apertures are opposed to each other to form a cross channel across the hole.

The disclosure also includes locking devices for holding a suture in tension, that include a housing member having a hollow interior with a first end having a first hole, a second end having a second hole, and a side wall having at least one side opening and a flat portion away from the at least one side opening, the housing member having a longitudinal axis. A pin member having a shaft, a gripping portion in the form of a flange at a first end of the shaft, and a bulbous tail portion at a second end of the shaft having an external diameter greater that a diameter of the second hole, is positioned so that the flange is within the hollow interior of the housing member and the shaft is along the longitudinal axis and at least partially within the hollow interior. The flange is movable along the longitudinal axis within the hollow interior and is just slightly smaller in diameter than an inner surface of the hollow interior so that a suture can be pressed between the flange and the inner surface. The bulbous tail portion can include a groove parallel to the longitudinal axis and aligned with the flat surface of the housing member. A spring is within the hollow interior and around the shaft, the spring engaging the flange and biasing the flange toward the first end of the housing member. The shaft of the pin member can include a first transverse hole located between the tail portion and the flange, the first transverse hole adapted to accommodate a portion of a triggering mechanism that will maintain the pin member in a retracted condition against the bias of the spring when present in the first transverse hole and outside of the housing member. A second transverse hole can be located in the tail portion and adapted to accommodate a portion of a gripping or pulling mechanism for retracting the pin member against the bias of the spring.

In particular embodiments, a locking device according to this disclosure can be connected to a suture in many procedures, including those in which suture(s) are cinched to provide tension on an implant. Cinching the suture involves pulling it through the locking device (or holding the suture while the locking device is moved with respect to it), and quickly locking the locking device to hold the suture in tension. Some embodiments according to this disclosure also make release and/or adjustment (if needed) of the locking device and suture simpler.

DESCRIPTION OF THE ILLUSTRATED EMBODIMENTS

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the disclosure is thereby intended. Any alterations and further modifications in the described embodiments and any further applications of the principles of the present disclosure as described herein are contemplated as would normally occur to one skilled in the art to which the disclosure relates.

Referring generally to the drawings, there is shown an embodiment of a suture lock 20 including a housing 22, a distal cap or sleeve 24, and a spring-biased locking pin 26. "Distal" as used herein refers to a direction generally away from the operator and/or generally toward a surgical location, and "proximal" as used herein refers to a direction generally toward the operator and/or generally away from the surgical location. Housing 22 and sleeve 24 cooperate to form an inner chamber 28 that houses the locking pin 26.

Figure 1:
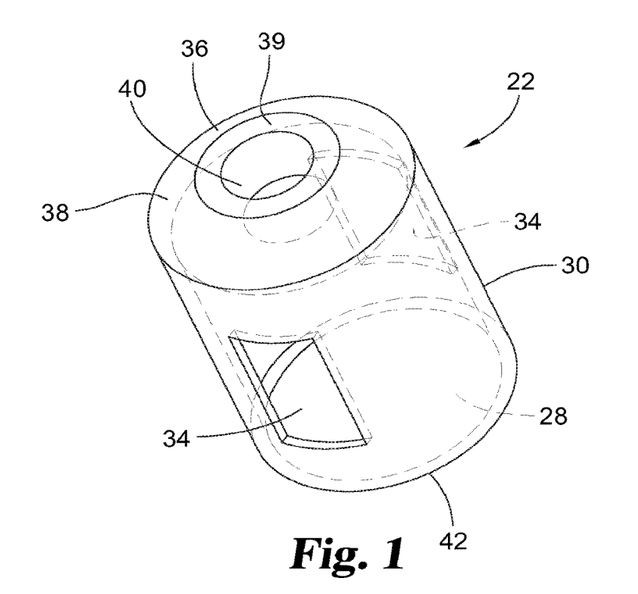
FIG. 1 is a perspective view of an exemplary embodiment of a housing for an embodiment of a suture lock.

Housing 22 may be substantially cylindrical (FIG. 1), with a circular side wall 30 with a pair of opposing side openings 34. The side openings 34 allow a suture S to pass out of housing 22, and it will be understood that in other embodiments such openings may be located in other parts of housing 22 and/or cap 24, such as on a proximal end 36 of the housing. Openings 34 in an illustrated embodiment are generally rectangular (e.g. square) with rounded corners in the side wall 30 of housing 22. Openings 34 are opposite to each other (e.g. with centers positioned 180 degrees apart) in a particular embodiment. End 36 of housing 22 has a rounded end surface 38 joining with side wall 30 and a central flat surface 39 around a central hole 40. Hole 40 is sized and configured for accommodating a shaft part of locking pin 26. End 42 of housing 22 is open within side wall 22, in this example.

Figure 2:
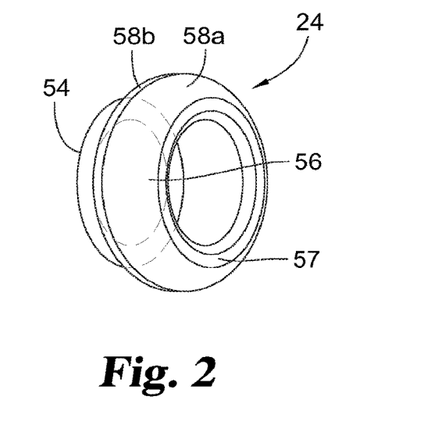
FIG. 2 is a perspective view of an exemplary embodiment of a cap or sleeve for an embodiment of a suture lock.

Cap 24 covers end 42 of the housing, and in this embodiment is partially inserted into and is fixed to housing 22, as by welding, soldering, crimping, interference fit, threading, adhesive attachment, or other fixation method. A skirt or flange portion 54 of cap 24 is inserted into housing 32 so that skirt 54 engages the inside wall of housing 22. In particular embodiments, skirt 54 and/or an adjacent surface of cap 24 facing housing 22 is fixed to housing 22 by threads, welding, adhesives, or other physical or chemical joining, to ensure the cap 24 is secured to housing 22. It will be understood that in other embodiments the cap 24 could be part of housing 22 (e.g. monolithic or integrated). In addition to portion 54 inserted into housing 22, cap 24 includes a central opening 56 that in this embodiment is larger than the hole 40 in the proximal end surface 36 of the housing 22, to accommodate at least part of a head portion of the locking pin 26. A flat surface 57 surrounds opening 56 in the illustrated embodiments, with a rounded exterior surface 58a around flat surface 57 and extending to a boss 58b that adjoins skirt 54 and engages housing 22.

Figure 3:
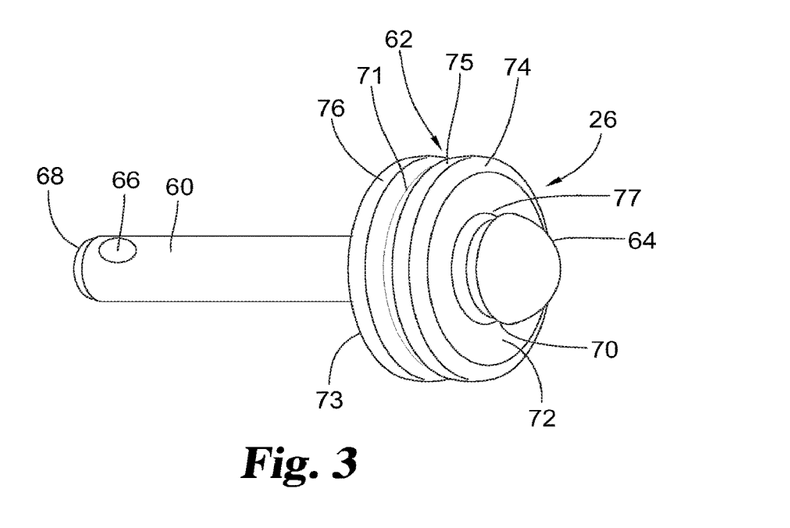
FIG. 3 is a perspective view of an exemplary embodiment of a locking pin for an embodiment of a suture lock.

The illustrated embodiment of the locking pin 26 includes a cylindrical shaft 60, a gripping portion in the form of a radially-extending disc or flange portion 62 in this embodiment, and a head portion 64. The shaft 60 includes a through hole 66 at or near its end 68 opposite from the head 64, which is perpendicular to the longitudinal axis of shaft 60 in this example. The hole permits attachment of a wire, filament or other structure to allow pulling of the locking pin against a spring 70 and/or release of locking pin 26 to be forced forward by spring 70. The disc or flange 62 is between shaft 60 and the head 64, and includes a central circumferential groove 71 evenly spaced between opposite flat surfaces 72, 73 of flange 62. Flange 62 includes a rounded or part conical surface 74 that extends from surface 72 to an edge portion 75, which is the outer diameter of flange 62. A second edge portion 76, which in one embodiment is thicker than edge portion 75 as measured parallel to the longitudinal axis of shaft 60, adjoins or is adjacent to surface 73. Edge portions 75 and 76 bracket groove 71.

The head portion 64 is part spherical in this embodiment, and joins the flange 62 via another circumferential groove 77 between a lip or edge 78 of the part spherical surface of head 64 and surface 72 of flange 62. Groove 77 has a minimum outer diameter greater than the diameter of the shaft 60 but less than the outer diameter of groove 71 in flange 62 in this embodiment. Such grooves, or other grooves or protrusions in the locking pin 26, sleeve 24 or housing 22, help to grip the suture(s) passing over or around them. For example, the grooves and surfaces in the illustrated embodiment are provided in order to force the suture to make multiple (e.g. three-point) bends when the locking pin 26 advances into the sleeve 24. The bends, where the suture S engages one or more of edges 75, 76, 78 enable lock 20 to have much greater gripping and/or tensile strength than can be achieved with purely friction or pinching locking mechanisms.

The flange 62 is sized such that its outer diameter is slidable inside chamber 28 of housing 22 yet close enough to an inner diameter of chamber 28 so that a suture can be gripped or pinched between at least part of flange 62 and the inner wall of housing 22. The outer diameter of flange 62 is larger than the opening 56 in the cap or sleeve 24, and equal to or larger than the inner diameter of the spring 70, such that the flange 62 cannot move past the sleeve 24 and the spring 70 cannot slip past the flange 62. In a particular embodiment, the outer diameter of head portion 64 is slidable into opening 56 of cap 24, yet close enough in size to an inner diameter of opening so that a suture can be gripped or pinched between at least part of head 64 and cap 24. Certain regions of the locking pin 26, for example the proximal part of shaft 60, could have an outer diameter smaller than the inner diameter of the spring 70 such that part of the pin 26 can pass through the spring 70.

The spring 70 lies entirely within the housing 22 and around shaft 60 of pin 26, with the sleeve 24 at the distal end 42 of the housing 22. The spring 70 is located in the inner chamber 28 formed by the housing 22 and sleeve 24, between the flange 62 of the locking pin 26 and the proximal inside surface of the housing 22 that faces the flange 62. The spring 70 must be compressed to fit between the flange 62 and the inside surface of the housing 22, so that it biases the locking pin 26 toward the sleeve 24.

In some embodiments, plunger shaft 60 is hollow, having a lumen 79 extending between openings 80 and 82 in the respective ends of shaft 60. Lumen 79 provides a path for passage of pieces related to lock 20 and/or to a medical device associated with and/or locked by lock 20. For example, lumen 79 may allow passage of a delivery wire, over which lock 20 and/or other parts of an assembly may be moved through a sheath or otherwise, to a location for implantation. Once placed, the delivery wire can be easily withdrawn through lumen 79 to allow lock 20 to remain at the implantation site.

Figure 5:
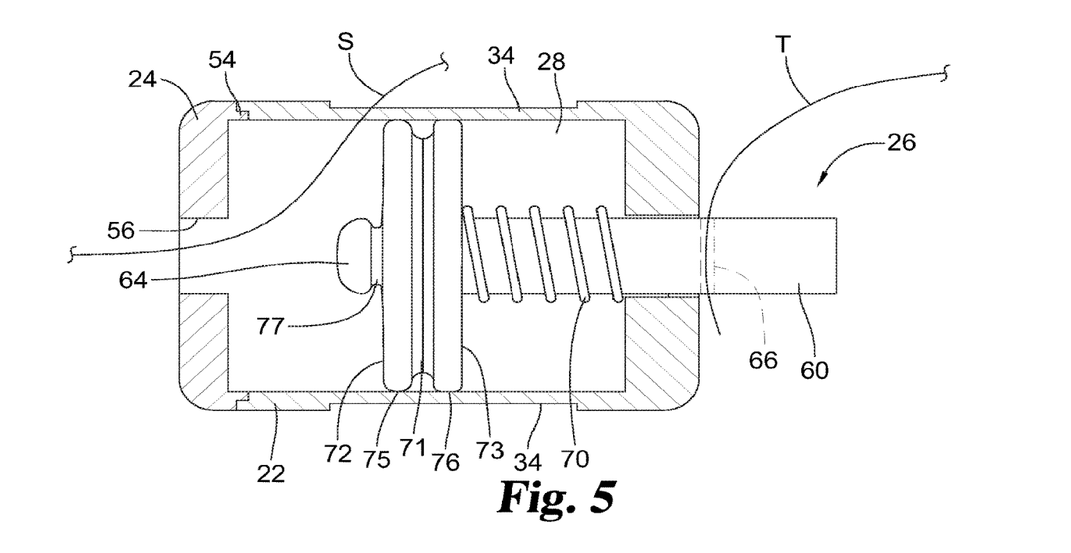
FIG. 5 is a part cross-sectional view of the embodiment of FIG. 4 in an initial or unlocked condition.

To use the device 20, the user retracts the locking pin 26, as by pulling on shaft 60 or a filament through the hole 66 in shaft 60. The locking pin 26 may remain retracted by maintaining tension on it and/or by placing a line (e.g. a metal wire), rod, plug or other block (shown schematically as T in FIG. 5) through the hole 66 in the shaft 60. Such a line or block engages end 42 of housing 22 when pin 26 is under the bias of spring 70, to prevent the locking pin 26 from moving fully forward (e.g. so that the surface of flange 62 facing cap 24 engages cap 24, and/or flange 62 moves past openings 34 in housing 22). For instance, a trigger line or wire may be placed in the through hole 66 in the proximal end of the shaft 60, maintaining the pin 26 in an unlocked position. Removing the trigger wire allows the pin 26 to advance within housing 22 under the influence of spring 70 to the locked position. It will be understood that the user can retract the pin 26 in a number of ways. For example, a female thread may be provided on the proximal end of the shaft 60, to which a drive wire or cable is connected. Turning or otherwise operating the drive wire or cable moves the locking pin against the bias of spring 70. As another example, the proximal end of the shaft 60 could be grasped by a snare, at a groove or a protrusion on the shaft 60 to enable grasping, and retracted.

Figure 4:
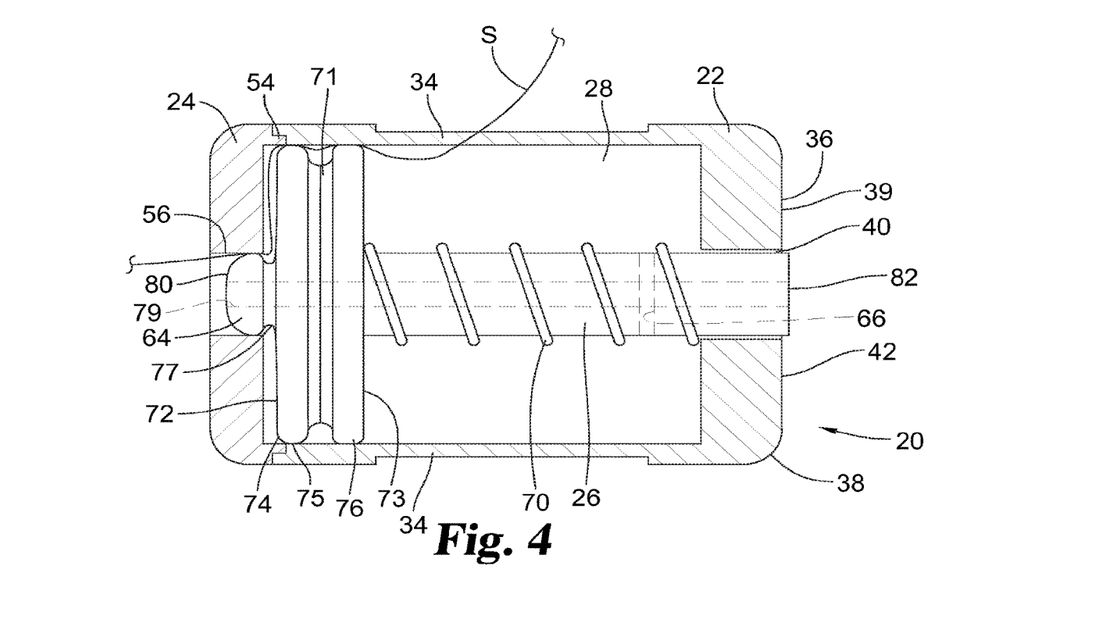
FIG. 4 is a part cross-sectional view of an exemplary embodiment of a suture lock using the embodiments of FIGS. 1-3, in a locked condition.

In its initial condition (e.g. FIG. 5), pin 26 is retracted and held as noted above, and a suture S extends through housing 22. Although one suture S is shown in the drawings, it will be understood that one or more such sutures may be locked with lock 20. In the illustrated embodiment, suture S passes through (entering or exiting) hole 56 in cap 24, passes the head portion 64 and flange 62 of the locking pin 26 within housing 22, and passes through (exiting or entering) one or both of openings 34 in housing 22. The user moves the lock 20 (e.g. through a catheter and/or via a placement instrument) to the desired location, preferably traveling along, over or with a portion of suture S. Once at the desired location, e.g. adjacent an implant that uses suture S, the user may apply any desired tension to the suture. When properly positioned and locking of the suture is desired, the locking pin 26 is released, as by removing a line or block through hole 66 of shaft 60. The bias of the spring 70 forces the locking pin 26 forward so that suture S is held or pinched between one or more edges of the flange 62 and/or head 64 of pin 26, and the adjacent sleeve 24 and/or housing 22 surfaces (e.g. FIG. 4). The suture(s) may be gripped by the flange 62 at three-point bends created by one or more of the grooves 71, 77 or adjoining surfaces of the locking pin 26. The grip on the suture(s), potentially at multiple locations and sustained by the spring bias, thus locks the suture(s) in place.

Among advantages that have been considered over prior suture locking devices, embodiments of the present device require no force to be applied against the suture by the user to lock it. The user simply needs to release the locking pin 26 (as by pulling or otherwise removing a trigger wire holding pin 26 against bias of spring 70) and the suture is automatically locked. The pressure applied to the suture by the locking pin 26, and thus the locking strength, is controlled by the force of spring 70, not by how hard the user pressed the pin 26 into the sleeve 24 or along housing 22. Also, the locking force is applied directly at the locking site and from the position of the user, so better force transmission to the pin 26 is achieved. Further, the spring-loaded locking device is more resistant to unlocking. In situations such as vibrations or pulsatile forces on the suture, it is possible that a pin or other holder could become dislodged from a sleeve or housing. Having pin 26 held in place by spring 70 ensures that the device remains in the locked position.

Other embodiments of a suture lock are also contemplated. In the discussion below, numbers having their final two digits identical to numbers or the final two digits of numbers above are similar or identical to parts discussed above.

Figure 6:
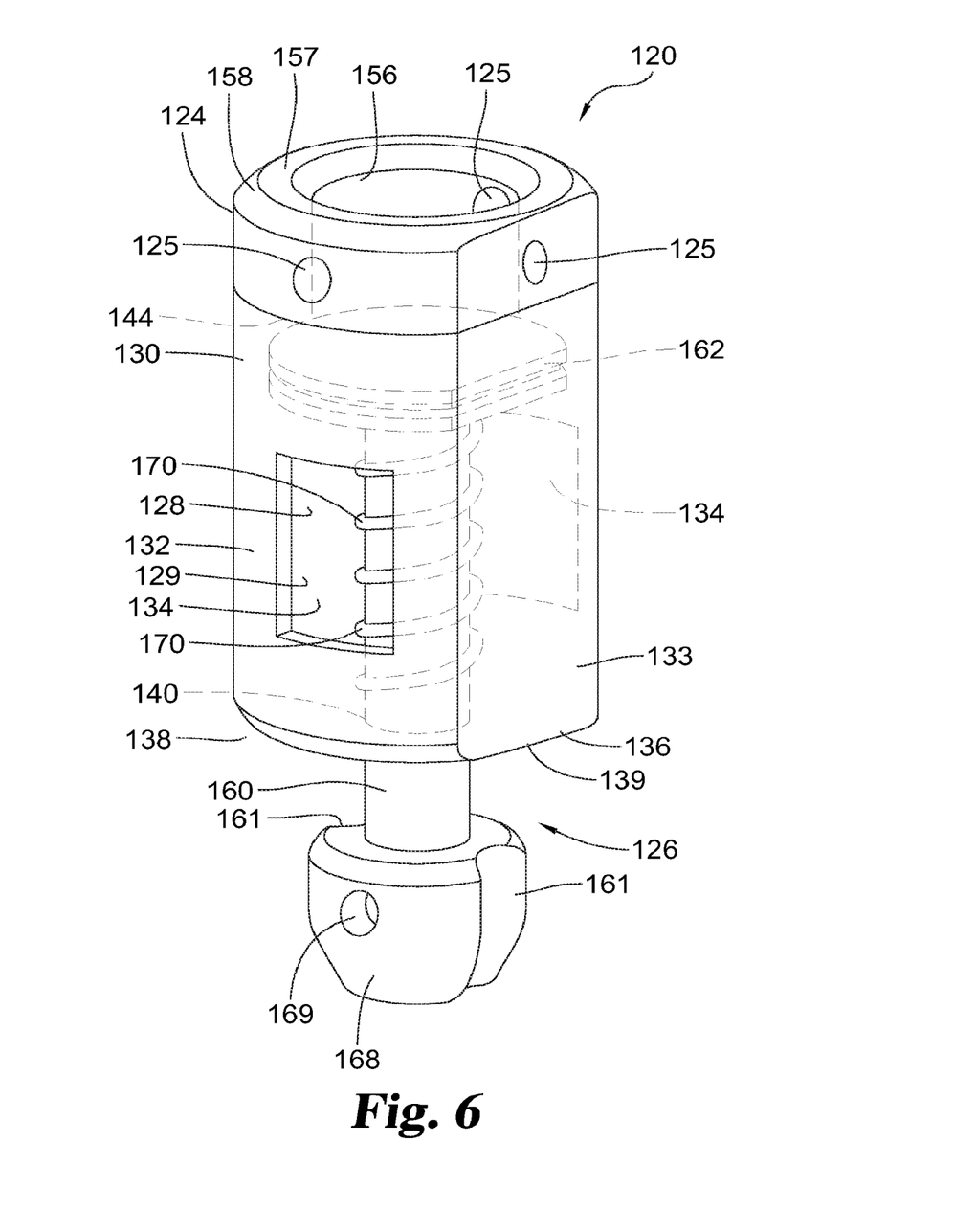
FIG. 6 is a perspective view of an exemplary embodiment of a suture lock.

Lock 120 includes a housing 122, and a spring-biased locking pin 126. Housing 122 is a hollow body with a longitudinal axis along or parallel to which pin 126 travels. An external wall 130 has a circular portion 132 and a planar portion 133, so that housing 122 is at least approximately D-shaped in cross-section perpendicular to the longitudinal axis. The circular side wall portion 132 includes a pair of opposing side openings 134, which allow one or more sutures to pass through into and/or out of housing 122 as described above. A distal end 124 (which may be a cap or sleeve joined to a main housing, as discussed above with respect to lock 20) and a proximal end 136 of the housing 122 are provided. Openings 134 in an illustrated embodiment are generally rectangular (e.g. square) with rounded corners in the side wall portion 132 of housing 122. Openings 134 are opposite to each other (e.g. with centers positioned 180 degrees apart) in a particular embodiment. As seen in FIG. 6, openings 134 are 90 degrees offset from the center of planar wall portion 133. End 136 of housing 122 has a rounded end surface 138 joining with side wall 132 and a central flat surface 139 around a central hole 140 in particular embodiments. Hole 140 is sized and configured for accommodating a shaft part of locking pin 126. End 124 of housing 122 is open within side wall 132, in this example.

Distal end 124 of housing 122 abuts or connects to cylindrical surface 132 and planar flat surface 133. It has a hole 156 which is circular, and extends to within the cylindrical and planar exterior portions of housing 122, and communicates with chamber 128 of housing 122. The inner diameter of hole 156 is smaller than outer diameter of flange 162 of pin 126 at its greatest. End 124 has a flat end surface 157 surrounding opening 156, with rounded surface(s) 158 joining flat end surface 157 with rounded wall portion 132 and flat portion 133. Holes 125 are provided in end 124, each being perpendicular to the longitudinal axis of housing 122 in the illustrated embodiment. One hole 125 is through flat portion 133, and three holes 125 are through rounded portion 132 in this embodiment, with 90 degrees separating adjacent holes 125 as one example. Apertures 125 may be perpendicular to the longitudinal axis of housing 122, and may be in opposed pairs that form one or more cross-channels. One or more apertures 125 or cross-channels formed by them may be used to guide a suture through lock 120, for holding or controlling by an external line or wire, or for other purposes.

Housing 122 in this embodiment has an open internal chamber or volume 128 extending between hole 140 in end 136 and end 124. Chamber 128 is hounded or at least partially bounded by an internal surface 129 of wall 130, through which side openings 134 extend. Internal surface 129 may be D-shaped, corresponding to the exterior shape of housing 122 (e.g. wall 130 has a constant thickness in chamber 128), or may be cylindrical even adjacent flat portion 133 of housing 122, so that the wall thickness of housing 122 is smallest in the middle of flat portion 133, and increases to either side to a constant thickness in rounded wall portion 132. Seat portion 144 is a boss or curved surface between side openings 134 and surface 158, and presents one or more locations for pinching a suture between housing 122 and pin 126. It will be understood that seat 144 may be flat (e.g. FIG. 6), conical (e.g. surface 129 narrowing) or curved (144" of housing 122" in FIG. 9), or sloped.

Figure 7:
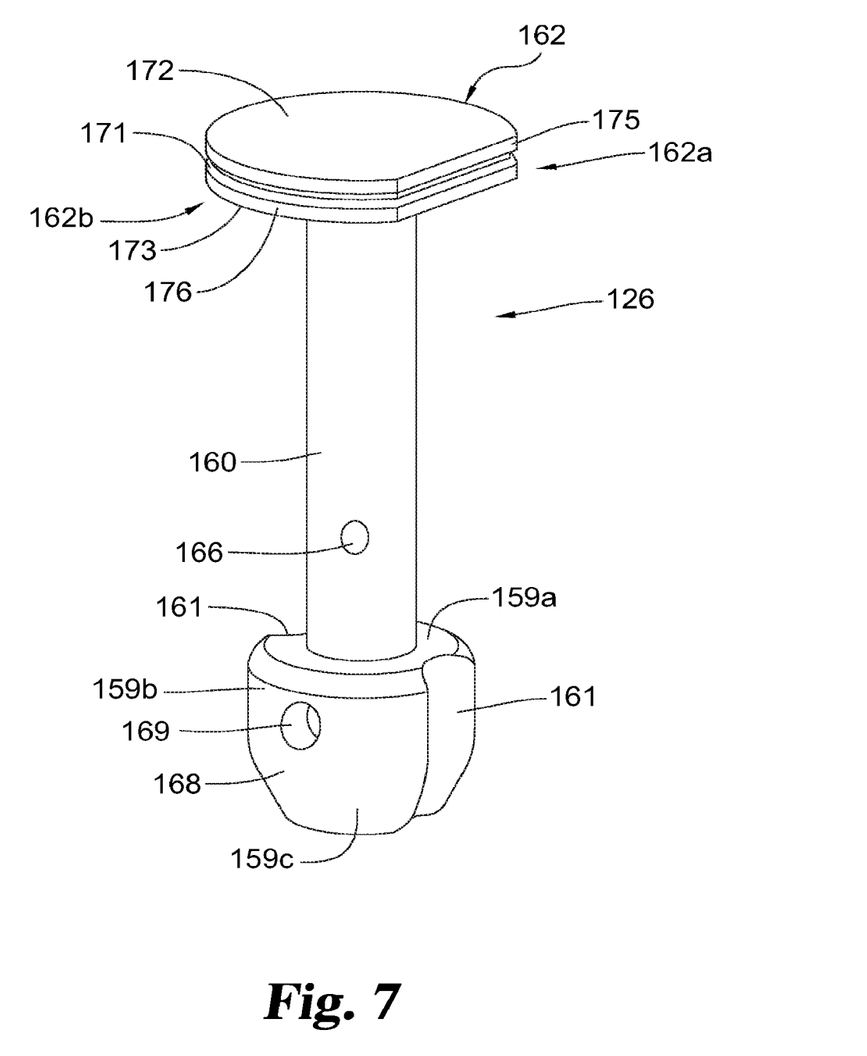
FIG. 7 is a perspective view of an exemplary embodiment of a locking pin in the embodiment of FIG. 6.

Locking pin 126 in this embodiment includes a cylindrical shaft 160, a gripping portion in the form of a disc or flange 162 at one end, and a bulbous opposite end or tail portion 168. Shaft 160 is a cylinder in this embodiment, and is monolithic with or joined to flange 162 and bulbous tail portion 168. In the illustrated embodiment, flange 162 is at one end of shaft 60, and includes a flat portion 162a of the circumference with a cylindrical portion 162b. A central circumferential groove 171 is evenly spaced between opposite flat surfaces 172, 173 of flange 162, with surface 172 facing away from tail portion 168, and surface 173 facing toward tail portion 168. Flange 162 includes edge portions 175 and 176, which are the outer diameter or extent of flange 162. Edge portions 175 and 176 may be as described above with respect to edges 75, 76 of flange 62, and may include rounded or part conical surfaces as described above with respect to flange 62. Edge portions 175 and 176 bracket groove 171. Flange 162 is sized such that its outer diameter is slidable inside chamber 128 of housing 122 yet close enough to an inner diameter of chamber 128 so that a suture can be gripped or pinched between at least part of flange 162 and the inner surface 129 of housing 122. The outer diameter of flange 162 is larger than the opening 156 in end 124, and equal to or larger than the inner diameter of the spring 170, such that the flange 162 cannot move past end 124 and the spring 170 cannot slip past the flange 162. Certain regions of the locking pin 126, for example the proximal part of shaft 160, could have an outer diameter smaller than the inner diameter of the spring 170 such that part of the pin 126 can pass through the spring 170. Shaft 160 includes a through hole 166 in for a trigger line or block, as described above with respect to hole 66 of lock 20.

Tail portion 168 is larger in diameter than shaft 160 in this embodiment. Tail portion 168 has a curved exterior, for example spherical or spheroidal in this embodiment. As a particular example, tail portion 168 has a flat surface 159a around shaft 160 facing housing 122, a cylindrical portion 159b extending from surface 159a, and a part spherical end portion 159c. Cylindrical portion 159b has the largest diameter in this embodiment and is smaller than the proximal hole 140 in housing 122. Through hole 169 extends through bulbous end 168, e.g. through cylindrical part 159b. Hole 169 is for threading through or other engagement of a wire, hook or other part of a pulling mechanism (not shown), so as to allow later retraction of pin 126 to adjust or remove device 20. Through hole 169 is perpendicular to the longitudinal axis of shaft 160 (and housing 122) in this example.

The illustrated embodiment includes two longitudinal broad grooves or channels 161, parallel to shaft 160 and to surface 133 of housing 122 when lock 120 is assembled. A groove 161, if present, may be aligned or on the same side as flat surface 133 with respect to housing 122 and flat side 162a of flange 162 (if present). Groove(s) 161 and flat surface 133 provide the advantage of allowing lock 120 to move along a wire or other guide, or allowing structure to move past lock 120, while maintaining a smaller yet sturdy outer diameter. For example, in a minimally-invasive or vascular-access procedure, when structures are placed or located in a catheter at or near a treatment site, remedial or other tools may be provided with lock 120 or may thereafter be needed. These features of lock 120 allow passage of such tools with limited disturbance of lock 120, a delivery catheter in which lock 120 sits, or adjacent tissue if lock 120 has been placed.

A spring 170 is connected to pin 126, e.g. around shaft 160, to bias pin 126 toward end 142 and flange 162 into contact with seat portion 144 of wall surface 129. Spring 170 is arranged as described above with respect to spring 70, so that shaft 160 is held against the bias of spring 170 to allow a suture or other piece to move through lock 120. The spring 170 lies entirely within the housing 122, e.g. in the inner chamber 128 formed by the housing 122. The spring 170 must be compressed to fit between side 173 of flange 162 and the inside surface around hole 140 of the housing, so that it biases the locking pin 126 toward end 142.

Configuration and use of lock 120 with one or more sutures is essentially the same as described above with respect to lock 20. In its initial condition, pin 126 is retracted and held as noted above, and a suture (not shown) extends through housing 122, e.g. passing through (entering or exiting) hole 156 (and perhaps one or more apertures 125) in end 124, passing flange 162 of locking pin 126 within housing 122, and passing through (exiting or entering) one or both of openings 134 in housing 122. The user moves the lock 120 (e.g. through a catheter and/or via a placement instrument) to the desired location, preferably traveling along, over or with a portion of the suture(s). Once at the desired location, e.g. adjacent an implant that uses the suture(s), the user may apply any desired tension to the suture(s). When properly positioned and locking of the suture is desired, the locking pin 126 is released, as by removing a line or block through hole 166 of shaft 160. The bias of the spring 170 forces the locking pin 126 forward so that the suture(s) is held or pinched between one or more edges of the flange 162 of pin 126, and the adjacent surfaces (e.g. surface 129 and/or seat 144) of housing 122. The suture(s) may be gripped by the flange 162 at three-point bends created by one or more of the grooves 171 or 177. The grip on the suture(s), potentially at multiple locations and sustained by the spring bias, thus locks the suture(s) in place.

Lock 120, as indicated previously, may be easier in some minimally-invasive or vascular-access procedures to transport to a desired site because it requires a relatively smaller catheter or other delivery device to accommodate both lock 120 and a guide due to the presence of groove(s) 161 and flat surface 133. If additional tools or structure are needed at the treatment site, they may be passed by lock 120 through or adjacent groove 159 and flat surface 133, so as to avoid substantial disturbance to lock 120 and/or adjacent treatment structure or tissue. If adjustment or removal of lock 120 is necessary, a tool (e.g. a hooking or gripping tool) may be connected to pin 126, as by gripping tail portion 168 or moving through hole 169, to allow retraction of pin 126 and extraction or adjustment of lock 120 and/or the suture or device it locks. Even if additional tools or structure are not needed, the planar surface permits closer proximity and/or less likelihood of damage to or interference with an organ or other tissue.

Figure 8:
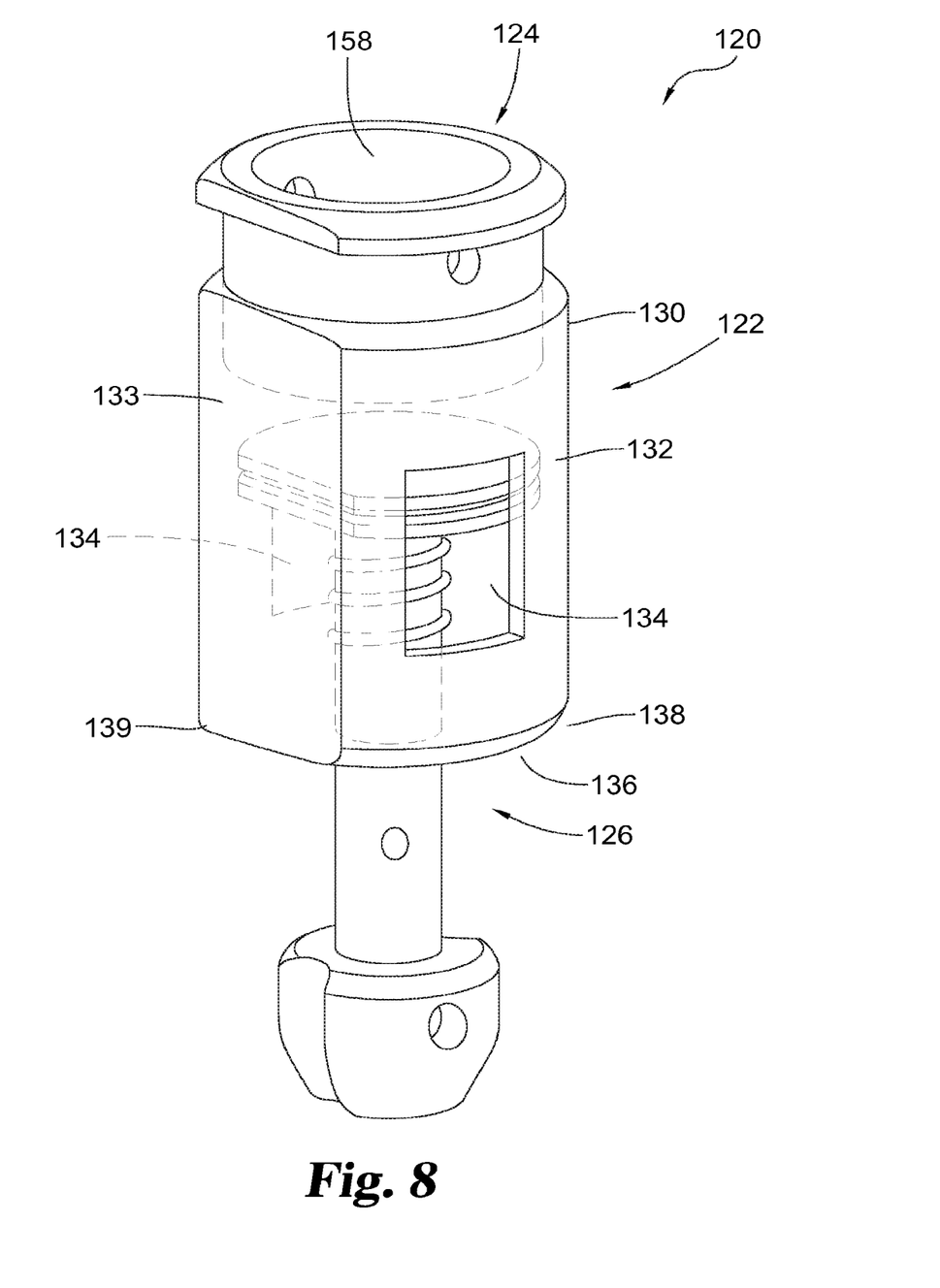
FIG. 8 is a perspective view of the embodiment of FIG. 6 with an alternative embodiment of a housing.

FIG. 8 shows a variation of lock 120. Lock 120' has a variation in housing 122' and otherwise is the same as lock 120. Housing 120' has an end 124' that includes a cylindrical portion 124a' through which apertures 125 extend, and a lip 124b'. Cylindrical portion 124a' is between lip 124b' and the rest of housing 122'. Lip 124b' has a circular portion 127a' and a flat portion 127b', which is planar with the surface 133 of housing 122'. In particular embodiments, lip 124b' has the same exterior side configuration as the rest of housing 122'. Cylindrical portion 124a' has a smaller outer diameter than lip 124b', and provides a location for a gripping tool for manipulating or holding lock 120', and/or an indicator of or some assistance to the user to access apertures 125.

Figure 9:
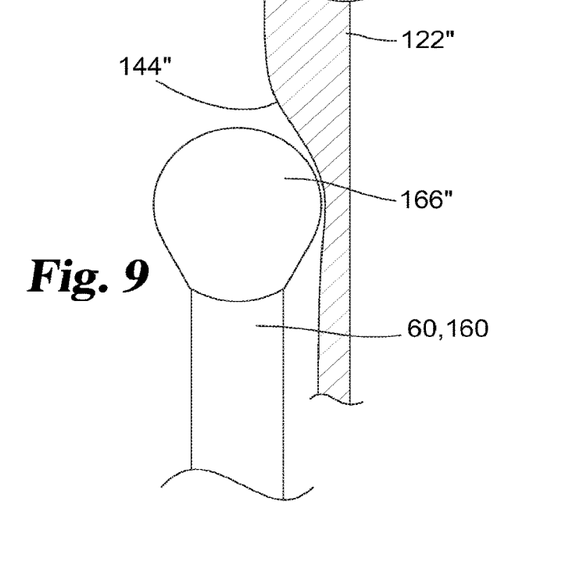
FIG. 9 is a part cross-sectional view of an alternative embodiment of structures in an exemplary embodiment of a suture lock.

FIG. 9 shows a variation of locking pin 126', having a gripping portion in the form of a bulbous head 162" in place of flange 162, and a conical wall or seat portion 144" inside of a housing 122". The bulbous head 162" and seat 144" provided a smooth, close fit to press a suture and hold it. These features may be incorporated into or used with embodiments as noted above.

Figure 10:
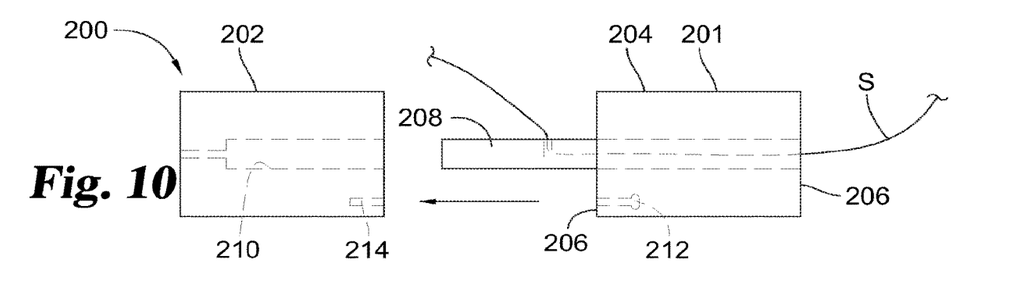
FIG. 10 is a side exploded view of an exemplary embodiment of a suture lock.
Figure 11:
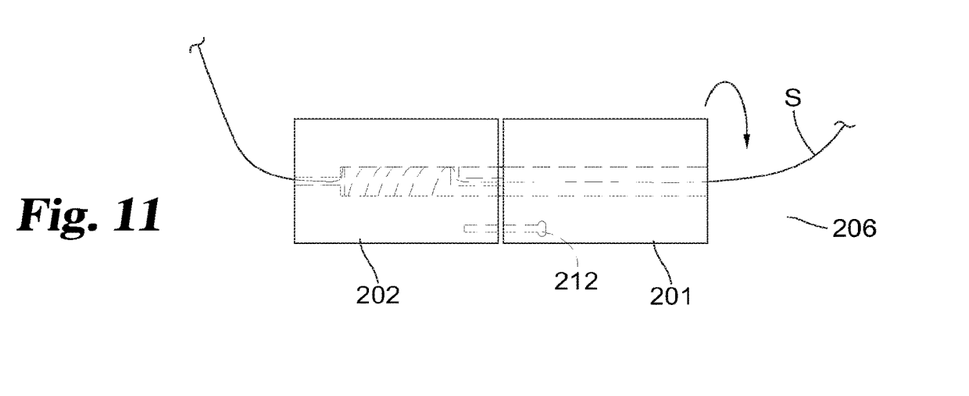
FIG. 11 is a side assembled view of the embodiment of FIG. 10.

Other embodiments for locking a suture, wire or other filament are disclosed herein. In FIG. 10-11, there is shown an embodiment of a suture lock 200 including a first barrel 201 and a second barrel 202 connected together so that they can rotate with respect to each other. First barrel 201 is a cylindrical piece in a particular embodiment having a side wall 204 and two end walls 206. A shaft 208 extends from one of the end walls 206. Second barrel 202 is of the same or similar size and external configuration as first barrel 201, and includes a central cylindrical passage or lumen 210 to accommodate shaft 208 of first barrel 201. In this embodiment, shaft 208 has an outer diameter that is less than the inner diameter of lumen 210, so that a filament can be wrapped around shaft 208 within lumen 210.

A locking pin 212 is connected with one of the barrels (first barrel 201 in FIGS. 10-11), and the other barrel (second barrel 202 in FIG. 10-11) has one or more corresponding locking openings 214. Pin 212 is held in first barrel 201 in this embodiment against a spring bias via a trigger wire (not shown) so that pin 212 does not extend into opening 214. When pin 212 is held against the bias, barrels 201, 202 are able to turn with respect to each other around shaft 208. For example, the user may hold second barrel 202 and turn first barrel 201, so that shaft 208 turns within lumen 210.

The suture or other filament to be tightened is connected to lock 220 so that turning the barrels 201, 202 with respect to each other twists the filament around the shaft 208, increasing tension on the filament and winding the filament into a locking configuration. As one example, suture S passes through a channel 221 through barrel 201 and out through a side opening 223 in shaft 208, then through lumen 210 in barrel 202 to exit barrel 202. Alternatively, one end of suture S may otherwise be secured to shaft 208 or another part of first barrel 201, and extends through lumen 210 and out of an end opening or side opening of lumen 210.

In use, similar to the uses described above with respect to locks 20 and 120, a device using suture S is placed as desired in the body. Tension in suture S may be adjusted by pulling suture S, which can move through barrels 201, 201 (e.g. through lumen 210 and channel 221). When locking is necessary, first barrel 201 (in this example) is turned so that shaft 208 turns within lumen 210 of second barrel 202 (indicated by the arrow in FIG. 11). Suture S is wound around shaft 208 to maintain the tension on suture S and locks it, as by friction between windings of suture S and/or between suture S, shaft 208 and the wall around lumen 210. When the tightening or locking is sufficient, pin 212 is released to move forward under bias and into opening 214. With barrels 201, 202 unable to rotate with respect to each other, suture S is held and its tension is maintained.

Figure 12:
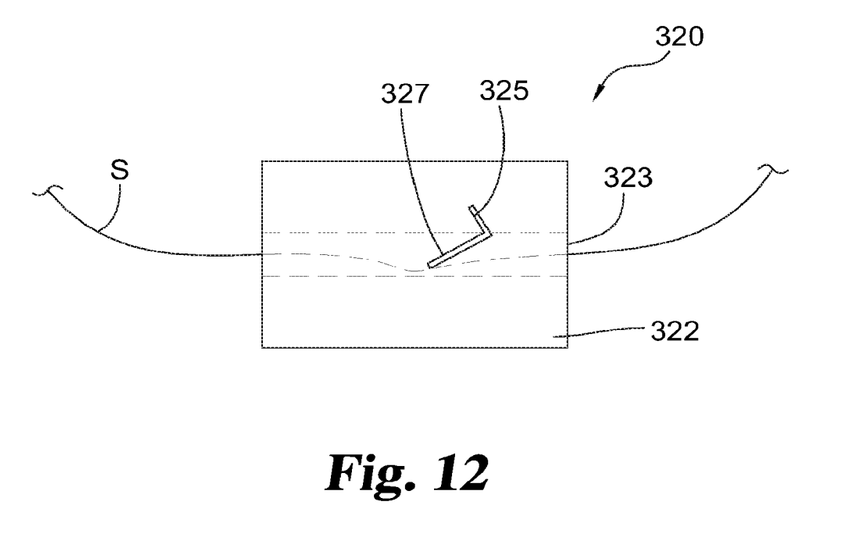
FIG. 12 is a schematic view of an exemplary embodiment of a suture lock.

In another embodiment, a filament is passed through a lock 320 that pinches the filament using a lever or cam. For example, as shown in FIG. 12, a body portion 322 of lock 320 has a passage 323 through which suture S travels. A cam or lever 325 is pivotably attached to body portion 322 so that a leg or surface 327 of cam or lever 325 is biased (e.g. via a spring, not shown) into passage 323. Similar to lock 220, lock 320 is moved with suture S associated with an implant into a treatment location. Suture S is then placed in tension as may be desired. As suture S is pulled in a tightening direction, cam or lever 325 permits the pulling, for example the pulling tends to turn cam or lever 325 against the bias. Cam or lever 325 prevents the filament from moving in an untightening direction by virtue of the bias and/or friction between the cam or lever 325 and the filament. Cam or lever 325 may have a rough surface 327 to increase such fiction when pinching suture S. In a particular embodiment, cam or lever 325 is held against its bias away from suture S during tightening, as by a trigger line or wire (not shown) as described above with respect to other embodiments, placed through or against cam or lever 325 similarly to the use of a trigger line or wire as described above. When the tension on suture S is as the user desires, the trigger line or wire may be pulled to release cam or lever 325 and allow it to be biased into contact with suture S and hold it. In another embodiment, in which cam or lever contacts suture S during tightening, allowing it to move in one direction but not in the other, such a trigger line or wire may be connected to cam or lever 325 to allow pulling of cam or lever 325 against a bias, thus allowing suture S to be moved in both directions relative to lock 320, if adjustments or removal are necessary.

It will be understood that cam or lever 325 may include or be replaced by first and second plates or surfaces each having mating contours that face each other. Such surfaces may be any of a number of surfaces that interact to increase friction, pinch or otherwise lock a suture between them, such as V- or W-shaped wedges, or an S-shaped contour on each surface or plate so that complementary surfaces on each surface or plate act together to pinch or press a suture between them. The plates or surfaces, as described with respect to one embodiment of lock 320, are held apart with respect to each other against a bias by a trigger wire (not shown), or can be moved together via a screw-drive mechanism (not shown). A suture is between the complementary surfaces or plates, and can be moved with respect to them to tightened or otherwise adjust the suture as the user desires. When it is desired to hold the suture in a desired position or tightness, the trigger wire is pulled to allow the bias to act on one or both plates or surfaces, pressing them together and engaging them with the suture filament to hold it between them.

Embodiments as disclosed herein may be used in any procedure or application in which sutures or other filaments need to be locked and/or maintained in a certain relationship with other structures or features. Specific applications of the device may include holding or locking sutures during or in completing Trans-auricular Intra-Pericardial Tricuspid Annuloplasty (TRAIPTA), gastrointestinal perforation closure, surgical access closure, tissue apposition (e.g. stomach plication), and others.

Embodiments may be made out of sturdy or rigid biocompatible plastics or metals. The spring could be made of spring steel, stainless steel, or Nitinol. The pieces could be assembled through laser welding, soldering, gluing, or snap fit geometries. The components could be made by machining, injection molding, or metal injection molding.

While the disclosure has been illustrated and described in detail in the drawings and foregoing description, the same is to be considered as illustrative and not restrictive in character, it being understood that only selected embodiments have been shown and described and that all equivalents, changes, and modifications that come within the spirit of the disclosures as defined herein or by the following claims are desired to be protected. It will be understood that features described particularly with respect to one or more specific structures or embodiments may be incorporated into or otherwise used with other structures or embodiments as disclosed herein.

The following numbered clauses set out specific embodiments that may be useful in understanding the present invention:

1. A locking device for holding a suture in tension, comprising:

a housing member having a hollow interior with an interior end surface, a side wall and a first and second end, wherein the side wall includes two opposed side openings;

a pin member partially within the hollow interior, the pin member including a gripping portion within the hollow interior, a shaft member fixed to the gripping portion, and a hole extending through the shaft member perpendicular to a longitudinal axis of the shaft member; and a spring within the hollow interior and around the shaft member, the spring abutting the gripping portion of the pin member and the interior end surface of the housing member, wherein the device has a first unlocked condition in which the pin member is retracted and held against bias of the spring and the gripping portion is at a first location within the housing to a movement path for the suture through the at least one of the side openings, around the gripping portion of the pin member and through the first end of the housing member, and in the first unlocked condition a portion of the shaft extends through the second end of the housing member, and a second locked condition in which the spring bias holds the pin member in a position in which the gripping portion is in a second position closer to the first end than the first position is to the first end, and which creates at least one pinch point between the gripping portion of the pin member and the housing member.

2. The device of clause 1, wherein the housing member includes a part-cylindrical exterior, with a flat surface extending from the first end to the second end.

3. The device of clause 2, wherein the side openings are opposed to each other, and the flat surface is between the side openings.

4. The device of any of clauses 1-3, wherein the pin member has a bulbous tail portion on the shaft member opposite to the gripping portion, the tail portion having a maximum diameter greater than an external diameter of the shaft member.

5. The device of clause 4, wherein the tail portion includes an exterior longitudinal channel.

6. The device of clause 5, wherein the exterior longitudinal channel is aligned with the flat surface of the housing.

7. The device of any of clauses 4-6, wherein the tail portion includes a through hole perpendicular to the longitudinal axis of the shaft member.

8. The device of any of clauses 1-7, wherein the gripping portion of the pin member has an external diameter larger than an external diameter of the shaft member, and the hollow interior of the housing member includes a chamber having an interior diameter that allows the gripping portion to travel longitudinally within the chamber.

9. The device of any of clauses 1-8, wherein the gripping portion is in the form of a flange, having opposite facing first and second surfaces, a circumferential groove between the first and second surfaces, a first edge between the circumferential groove and the first surface, and a second edge between the circumferential groove and the second surface.

10. The device of clause 9, wherein the flange includes a circular portion and a flat side, the flat side oriented toward the flat surface of the housing member.

11. The device of any of clauses 9-10, wherein the pin member further includes a head portion connected to the first surface of the flange and collinear with the shaft, the head portion having a lip, and wherein a second circumferential groove is between the lip and the first surface of the flange.

12. The device of any of clauses 1-8, wherein the gripping portion is a bulbous head.

13. The device of any of clauses 1-12, wherein the first end of the housing includes a hole along the longitudinal axis and communicating with the hollow interior, the hole having an inner diameter smaller than an outer diameter of the gripping portion, and wherein the first end of the housing includes a plurality of apertures perpendicular to the longitudinal axis and communicating with the hole.

14. The device of clause 13, wherein at least one of the apertures is in the flat surface of the housing.

15. The device of any of clauses 13-14, wherein at least two of the apertures are opposed to each other to form a cross channel across the hole.

16. A locking device for holding a suture in tension, comprising:

a housing member having a hollow interior with a first end having a first hole, a second end having a second hole, and a side wall having at least one side opening and a flat portion away from the at least one side opening, the housing member having a longitudinal axis;

a pin member having a shaft, a gripping portion in the form of a flange at a first end of the shaft, and a bulbous tail portion at a second end of the shaft having an external diameter greater that a diameter of the second hole, wherein the flange is within the hollow interior of the housing member and the shaft is along the longitudinal axis and at least partially within the hollow interior, and wherein the flange is movable along the longitudinal axis within the hollow interior and is just slightly smaller in diameter than an inner surface of the hollow interior so that a suture can be pressed between the flange and the inner surface, and wherein the bulbous tail portion includes a groove parallel to the longitudinal axis and aligned with the flat surface of the housing member; and a spring within the hollow interior and around the shaft, the spring engaging the flange and biasing the flange toward the first end of the housing member.

17. The device of clause 16, wherein the shaft includes a first transverse hole located in the shaft between the tail portion and the flange, the first transverse hole adapted to accommodate a portion of a triggering mechanism that will maintain the pin member in a retracted condition against the bias of the spring when present in the first transverse hole and outside of the housing member, and a second transverse hole located in the tail portion and adapted to accommodate a portion of a gripping or pulling mechanism for retracting the pin member against the bias of the spring.

The invention claimed is:

1. A locking device for holding a suture in tension, comprising:
    a housing member having a hollow interior with an interior end surface, a side wall and a first and second end, wherein the side wall includes two opposed side openings;
    a pin member partially within the hollow interior, the pin member including a gripping portion within the hollow interior, a shaft member fixed to the gripping portion, and a hole extending through the shaft member perpendicular to a longitudinal axis of the shaft member;
    a spring within the hollow interior and around the shaft member, the spring abutting the gripping portion of the pin member and the interior end surface of the housing member,
    wherein the device has a first unlocked condition in which the pin member is retracted and held against bias of the spring and the gripping portion is in a first position within the housing member to provide a movement path for the suture through the at least one of the side openings, around the gripping portion of the pin member and through the first end of the housing member, and in the first unlocked condition a portion of the shaft member extends through the second end of the housing member, and a second locked condition in which the spring bias holds the pin member in a position in which the gripping portion is in a second position closer to the first end than the first position of the gripping portion is to the first end, and which creates at least one pinch point between the gripping portion of the pin member and the housing member; and
    further wherein (a) the housing member includes a part-cylindrical exterior, with a flat surface extending from the first end to the second end, and/or (b) the first end of the housing member includes a hole along the longitudinal axis and communicating with the hollow interior, the hole in the first end having a diameter smaller than an outer diameter of the gripping portion, and the first end of the housing includes a plurality of apertures perpendicular to the longitudinal axis and communicating with the hole in the first end.

2. The device of claim 1, wherein the housing member includes the part-cylindrical exterior, with the flat surface extending from the first end to the second end.

3. The device of claim 2, wherein the side openings are opposed to each other, and the flat surface is between the side openings.

4. The device of claim 1, wherein the pin member has a bulbous tail portion on the shaft member opposite to the gripping portion, the tail portion having a maximum diameter greater than an external diameter of the shaft member.

5. The device of claim 4, wherein the tail portion includes an exterior longitudinal channel.

6. The device of claim 5, wherein the housing member includes the part-cylindrical exterior with the flat surface extending from the first end to the second end, and wherein the exterior longitudinal channel is aligned with the flat surface of the housing member.

7. The device of claim 4, wherein the tail portion includes a through hole perpendicular to the longitudinal axis of the shaft member.

8. The device of claim 1, wherein the gripping portion of the pin member has an external diameter larger than an external diameter of the shaft member, and the hollow interior of the housing member includes a chamber having an interior diameter that allows the gripping portion to travel longitudinally within the chamber.

9. The device of claim 1, wherein the gripping portion is in the form of a flange, having opposite facing first and second surfaces, a circumferential groove between the first and second surfaces, a first edge between the circumferential groove and the first surface, and a second edge between the circumferential groove and the second surface.

10. The device of claim 9, wherein the housing member includes the part-cylindrical exterior with the flat surface extending from the first end to the second end, and wherein the flange includes a circular portion and a flat side, the flat side oriented toward the flat surface of the housing member.

11. The device of claim 9, wherein the pin member further includes a head portion connected to the first surface of the flange and collinear with the shaft member, the head portion having a lip, and wherein a second circumferential groove is between the lip and the first surface of the flange.

12. The device of claim 1, wherein the gripping portion is a bulbous head.

13. The device of claim 1, wherein the first end of the housing includes the hole along the longitudinal axis and communicating with the hollow interior, the hole in the first end having an inner diameter smaller than an outer diameter of the gripping portion, and wherein the first end of the housing includes the plurality of apertures perpendicular to the longitudinal axis and communicating with the hole in the first end.

14. The device of claim 13, wherein the housing member includes the part-cylindrical exterior with the flat surface extending from the first end to the second end, and wherein at least one of the apertures is in the flat surface of the housing member.

15. The device of claim 13, wherein at least two of the apertures are opposed to each other to form a cross channel across the hole in the first end.

16. A locking device for holding a suture in tension, comprising:
    a housing member having a hollow interior with a first end having a first hole, a second end having a second hole, and a side wall having at least one side opening and a flat portion away from the at least one side opening, the housing member having a longitudinal axis;

a pin member having a shaft, a gripping portion in the form of a flange at a first end of the shaft, and a bulbous tail portion at a second end of the shaft having an external diameter greater that a diameter of the second hole, wherein the flange is within the hollow interior of the housing member and the shaft is along the longitudinal axis and at least partially within the hollow interior, and wherein the flange is movable along the longitudinal axis within the hollow interior and is just slightly smaller in diameter than an inner surface of the hollow interior so that a suture can be pressed between the flange and the inner surface, and wherein the bulbous tail portion includes a groove parallel to the longitudinal axis and aligned with the flat surface of the housing member; and a spring within the hollow interior and around the shaft, the spring engaging the flange and biasing the flange toward the first end of the housing member.

17. The device of claim 16, wherein the shaft includes a first transverse hole located in the shaft between the tail portion and the flange, the first transverse hole adapted to accommodate a portion of a triggering mechanism that will maintain the pin member in a retracted condition against the bias of the spring when present in the first transverse hole and outside of the housing member, and a second transverse hole located in the tail portion and adapted to accommodate a portion of a gripping or pulling mechanism for retracting the pin member against the bias of the spring.

18. A locking device for holding a suture in tension, comprising:

a housing member having a hollow interior with an interior end surface, a side wall between a first end of the housing member and second end of the housing member, wherein the side wall includes two opposed side openings, and wherein the first end includes a hole communicating with the hollow interior;

a pin member partially within the hollow interior, the pin member including a gripping portion within the hollow interior and a shaft member fixed to the gripping portion; and a spring within the hollow interior and around the shaft member, the spring abutting the gripping portion of the pin member and the interior end surface of the housing member, wherein the device has a first unlocked condition in which the pin member is retracted and held against bias of the spring and the gripping portion is in a first position within the housing member to provide a movement path for the suture, the movement path extending from at least one of the side openings through and out of the hole of the first end of the housing member, and a second locked condition in which the spring bias holds the pin member in a position in which the gripping portion is in a second position closer to the first end than the first position of the gripping portion is to the first end, and which creates at least one pinch point between the gripping portion of the pin member and the housing member; and wherein the hole has an inner diameter smaller than an outer diameter of the gripping portion.

19. The device of claim 18, wherein the housing member includes a part-cylindrical exterior, with a flat surface extending from the first end to the second end.

20. The device of claim 18, wherein the gripping portion is a flange.

21. The device of claim 20, wherein the flange has opposite facing first and second surfaces and a circumferential groove between the first and second surfaces.

* * * * *